United States Patent [19]

Sze et al.

[11] 4,009,214
[45] Feb. 22, 1977

[54] SEPARATION OF HYDROGEN FLUORIDE FROM HYDROGEN CHLORIDE GAS

[75] Inventors: Morgan C. Sze, Upper Montclair; John E. Paustian, Whippany, both of N.J.

[73] Assignee: The Lummus Company, Bloomfield, N.J.

[22] Filed: Apr. 25, 1975

[21] Appl. No.: 571,805

[52] U.S. Cl. .............................. 260/653.7; 423/488
[51] Int. Cl.$^2$ .................. C07C 17/15; C07C 17/38; C07C 7/08; C07C 7/22
[58] Field of Search ................. 260/653.7; 423/488

[56] References Cited
UNITED STATES PATENTS

| 3,140,916 | 7/1964 | Lowdermilk | 260/488 |
|---|---|---|---|
| 3,816,599 | 6/1974 | Kafes | 260/488 |

FOREIGN PATENTS OR APPLICATIONS 1,451,629   6/1966   France ............................... 423/488

OTHER PUBLICATIONS

B23,046, Jan. 1, 1975, Hyatt, 260/653.7.

*Primary Examiner*—D. Horwitz
*Attorney, Agent, or Firm*—Marn & Jangarathis

[57] ABSTRACT

Hydrogen chloride gas, containing hydrogen fluoride and/or silicon tetrafluoride, is contacted with calcium chloride supported on activated alumina, to separate the hydrogen fluoride and/or silicon tetrafluoride therefrom.

8 Claims, 1 Drawing Figure

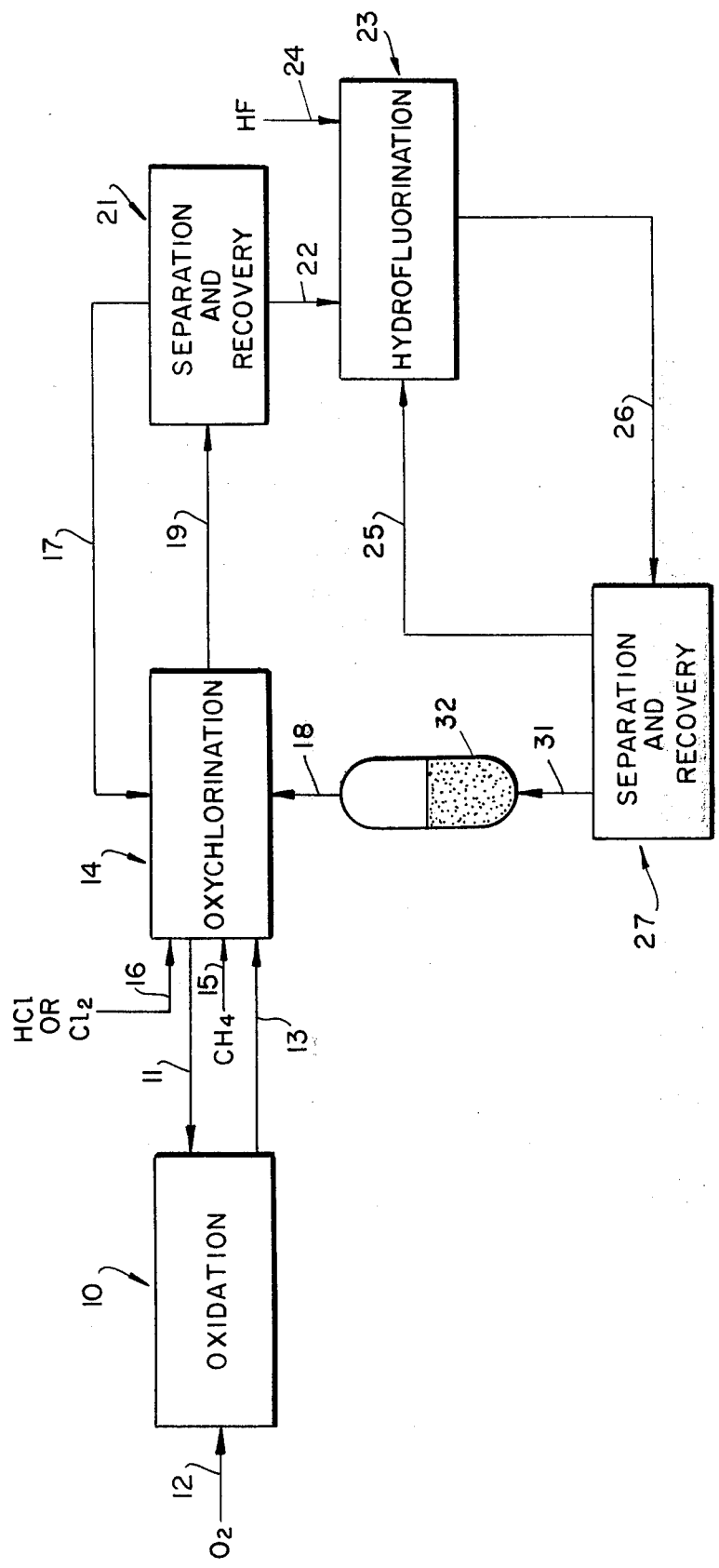

SEPARATION OF HYDROGEN FLUORIDE FROM HYDROGEN CHLORIDE GAS

The present invention is directed to the separation of hydrogen fluoride and/or silicon tetrafluoride from a gas stream and, more particularly, to the separation of hydrogen fluoride and/or silicon tetrafluoride from a gas steam containing hydrogen chloride and hydrogen fluoride and/or silicon tetrafluoride. This invention further relates to the production of chlorofluoromethanes.

The prior art discloses numerous techniques for separating hydrogen fluoride from a gas stream; however, such processes, in most cases, are not applicable to separating hydrogen fluoride and/or silicon tetrafluoride from gases containing hydrogen chloride in that the adsorbents employed also adsorb hydrogen chloride. As a result, the hydrogen chloride can displace or prevent retention of hydrogen fluoride on the adsorbent.

In many processes, there is produced a hydrogen chloride gas stream, which includes hydrogen fluoride and/or silicon tetrafluoride, as an impurity. Thus, by reaction of hydrogen fluoride with chlorinated methane(s) for example, in the production of chlorofluoromethanes, the hydrogen chloride generated in the process includes hydrogen fluoride as well as silicon tetrafluoride, which is introduced as an impurity in the hydrogen fluoride feed, and there is a need for an effective process for separating hydrogen fluoride and silicon tetrafluoride from such hydrogen chloride gas streams.

An object of the present invention is to separate hydrogen fluoride and/or silicon tetrafluoride from a hydrogen chloride gas.

Another object of the present invention is to remove hydrogen fluoride or silicon tetrafluoride from hydrogen chloride in an essentially dry system with no incidental addition of moisture.

A further object of the present invention is to separate hydrogen fluoride and silicon tetrafluoride from a hydrogen chloride recycle gas in a process for producing chlorofluoromethanes.

These and other objects should become apparent in reading the following description of the invention.

In accordance with the present invention, hydrogen fluoride and/or silicon tetrafluoride is separated from a hydrogen chloride gas stream by contacting the gas stream with calcium chloride supported on activated alumina. Applicants have found that the combination of calcium chloride and activated alumina provides an adsorbent and/or absorbent which can effectively separate hydrogen fluoride and/or silicon tetrafluoride from a hydrogen chloride gas, and which, in addition, has increased fluoride capacity.

The calcium chloride is generally employed in an amount from 1% to 30%, preferably from 5% and 15%, all by weight, based on activated alumina and calcium chloride.

The contacting of the gas with the activated alumina, containing calcium chloride, is generally effected at temperatures of from 0° C to 90° C, and preferably of from 10° C to 60° C. One of the distinct advantages of the present invention is that hydrogen fluoride and/or silicon tetrafluoride can be effectively separated at about room temperature.

The contacting is generally effected at pressures of from about 0 to about 450 psig, preferably from about 10 to about 150 psig. The contacting is effected for a time sufficient to reduce the hydrogen fluoride and/or silicon tetrafluoride to the required level. In general, contact times, as expressed in space velocities, are in the order of 10 to about 3000,GHSV, hr$^{-1}$, and preferably from about 40 to about 500. The contacting and adsorption can be effected under essentially anhydrous conditions.

The hydrogen chloride gas, employed as feed, in the present process generally contains hydrogen fluoride and/or silicon tetrafluoride each in an amount of from 50 to 1500 ppm. By proceeding in accordance with the present invention it is possible to reduce the hydrogen fluoride and silicon tetrafluoride contents each to less than 50 ppm, and preferably less than 5 ppm. It is to be understood that the hydrogen chloride gas can contain components other than hydrogen fluoride and/or silicon tetrafluoride.

The activated alumina, containing calcium chloride, is preferably utilized in the form of an upflow bed; however, it is to be understood that other means of effecting contacting between gas and solid adsorbent can also be employed. Thus, for example, contacting can be effected in a downflow moving bed or dilute phase transport reactor or a dense phase fluidized reactor.

The use of calcium chloride on activated alumina provides an adsorbent with increased fluoride capacity, in addition to the ability to effectively separate hydrogen fluoride and/or silicon tetrafluoride from a hydrogen chloride gas. In accordance with the present invention, it has been found that the fluoride capacity of the calcium chloride supported on alumina adsorbent may be as high as 30.0%, by weight.

In accordance with a preferred aspect of the present invention, the calcium chloride supported on alumina is employed for separating hydrogen fluoride and/or silicon tetrafluoride from a hydrogen chloride gas stream form a process for producing chlorofluoromethanes, and in particular, to purifying a hydrogen chloride recycle stream in a process for producing chlorofluoromethanes by the use of molten salts.

In accordance with the preferred aspect of the present invention, the separation of hydrogen fluoride and silicon tetrafluoride may be effected even in the presence of a small amount of fluorophosgene ($COF_2$) which may also be present as an impurity in the hydrogen chloride gas and which is also effectively removed.

The invention will be further described with respect to an embodiment thereof wherein the present invention is employed to remove hydrogen fluoride and silicon tetrafluoride from a hydrogen chloride recycle gas stream; however, it is to be understood that the scope of the invention is not to be limited thereto. The embodiment is illustrated in the drawing wherein:

The drawing is a simplified schematic flow diagram of a process for producing chlorofluoromethanes which incorporates the present invention.

Referring now to the drawing, a molten salt mixture containing the chlorides of a multivalent metal, in its higher and lower valence state, such as cuprous and cupric chloride and generally also including a melting point depressant, such as potassium chloride, is introduced into oxidation zone 10 through line 11, wherein the molten salt is contacted with molecular oxygen, introduced through line 12, to convert a portion of the cuprous chloride to copper oxychloride. The oxidation zone 10 is generally operated at temperatures of from 700° F to 950° F. A molten salt mixture of cuprous chloride, cupric chloride, copper oxychloride and, as a melting point depressant, potassium chloride, withdrawn from zone 10 through line 13, is introduced into oxychlorination zone 14 wherein the salt is contacted with fresh feed methane, introduced through line 15, fresh feed chlorine and/or hydrogen chloride, introduced through line 16 and recycle methane and chloromethanes, introduced through line 17 and recycle hydrogen chloride introduced through line 18. As a result, the methane is oxychlorinated to chloromethanes. The oxychlorination zone 14 is preferably operated at temperatures of from 700° F to 860° F.

An effluent, containing unreacted methanes substituted with from 1 to 4 chlorine atoms, heavier components, water vapor, carbon oxides, equilibrium amounts of hydrogen chloride, etc, is withdrawn from zone 14 through line 19, and introduced into a separation and recovery zone, schematically indicated as 21.

In the separation and recovery zone, the chloromethane(s) to be used as feed for the production of chlorofluoromethanes is separately recovered, and the remaining chloromethanes and unreacted methane are also recovered for recycle to zone 14 through line 17. As should be apparent, other chloromethanes could be recovered as separate product.

The chloromethane employed as feed to the hydrofluorination, is generally chloroform and/or carbon tetrachloride. For purposes of illustration, the feed shall be described as carbon tetrachloride.

Carbon tetrachloride recovered from zone 21, through line 22 is introduced into a hydrofluorination zone 23 along with hydrogen fluoride in line 24 and recycle components in line 25. The hydrofluorination zone 23 contains a suitable catalyst, such as molten antimony pentachloride, and is operated at conditions known in the art; e.g., temperatures in the order of 150° F to 300° F.

An effluent containing chlorofluoromethanes, in particular trichlorofluoromethane and dichlorofluoromethane, unreacted carbon tetrachloride and hydrogen chloride, withdrawn from zone 23 through line 26 is introduced into a separation and recovery zone 27 wherein carbon tetrachloride is recovered and recycled through line 25, chlorofluoromethanes are recovered as product through line 28 and hydrogen chloride is recovered for recycle to oxychlorination zone 14 through line 31.

The hydrogen chloride stream in line 31 also contains hydrogen fluoride and silicon tetrafluoride and in order to effectively recycle the hydrogen chloride, the hydrogen chloride gas should contain less than 50 ppm of hydrogen fluoride and silicon tetrafluoride. In accordance with the present invention, the hydrogen chloride gas in line 31 is passed through a bed of activated alumina, containing calcium chloride, in vessel 32, wherein the hydrogen fluoride and silicon tetrafluoride contents of the hydrogen chloride gas is each reduced to less than 50 ppm.

A recycle hydrogen chloride gas is withdrawn from vessel 32 through line 18 for introduction into oxychlorination zone 14. The invention will be further described with respect to the following examples, but it is to be understood that the scope of the invention is not to be limited thereto:

EXAMPLES

Example I. The absorbent, a γ-alumina containing 5 wt. % calcium chloride, was contained in a 1 O.D. × 14.5 inches long stainless steel tube. The HF-containing HCL was passed through at 70 psig, room temperature. After passing through the absorber, the exit gases were let down to atmospheric pressure and passed into scrubbers containing 4 moles NaOH. The time required for neutralization was used to calculate flow rates of the total acid gas stream, the neutral scrub solutions were analyzed for their fluoride contents using standard methods.

Analysis of the bed after these 210 hours of operation showed a 9.9%F content at the bed entrance and 0.1 wt.%F at the bed exit indicating the absorptive capacity of the bed had not yet been completely attained.

TABLE

| HF/HCl Charge No. | Initial HF Content, ppm | GHSV, hr$^{-1}$ | Time On Stream, hr. | Final HF Content, ppm |
|---|---|---|---|---|
| 1 | 400 | 43.8 | 4.4 | 10 |
| 2 | 575 | 43.8 | 31 | 4 |
| 3 | 308 | 37.7 | 65.6 | 4 |
| 4 | 317 | 53.8 | 100.7 | 4 |
| 5 | 1240 | 52 | 122.9 | 4 |
| 6 | 695 | 97 | 160.1 | 4 |
| 7 | 1240 | 99.7 | 179.2 | 4 |
| 8 | 1090 | 94.6 | 183.1 | 9.9 |

Example II. The absorbent bed of Example I was used to absorb $SiF_4$ from a HCl stream containing 135 ppm $SiF_4$. Adsorption took place at room temperature, a pressure of 70 psig, and a space velocity of GHSV 197 hr$^{-1}$. Analysis of the exit gases After 3 hours showed an $SiF_4$ content of less than 4 ppm.

The present invention is particularly advantageous in that hydrogen fluoride can be effectively removed from a hydrogen chloride gas. In addition, such removal can be effectively accomplished at low temperatures with an adsorbent of high fluoride retaining capacity.

Numerous modifications and variations of the present invention are possible in light of the above teachings and, therefore, within the scope of the appended claims, the invention may be practiced otherwise than as particularly described.

What is claimed is:

1. A process for separating an impurity from hydrogen chloride gas containing at least one member selected from the group consisting of hydrogen fluoride and silicon tetrafluoride, comprising:
  contacting at a temperature of from 0° to 90° C said hydrogen chloride gas with calcium chloride supported on activated alumina in an amount of from 1 to 30 weight percent based on activated alumina and calcium chloride to reduce the content of said at least one member to less than 50 ppm.

2. The process of claim 1 wherein the contacting is effected at a temperature of from 10° C; to 60° C.

3. The process of claim 1 wherein the contacting is effected under essentially anhydrous conditions.

4. The process of claim 3 wherein said impurity is hydrogen fluoride.

5. The process of claim 3 wherein said impurity is silicon tetrafluoride.

6. The process of claim 3 wherein said impurity is a mixture of silicon tetrafluoride and hydrogen fluoride.

7. The process of claim 3 wherein said contacting is effected at a space velocity of 10 to 3000 GHSV, hr$^{-1}$.

8. In a process for producing chlorofluoromethanes by oxychlorination of methane by contact with a molten salt mixture comprising the higher and lower valent chlorides of a multivalent metal and the oxychloride thereof and a member selected from the group consisting of hydrogen chloride, chlorine and mixture thereof to produce chlorinated methanes, contacting chlorinated methane with hydrogen fluoride to produce chlorofluoromethanes and hydrogen chloride and recovering hydrogen chloride containing an impurity selected from the group consisting of hydrogen fluoride and a mixture of hydrogen fluoride and silicon tetrafluoride, the improvement comprising:

contacting at a temperature of from 0° to 90° C the hydrogen chloride containing said impurity with calcium chloride supported on activated alumina in an amount of from 1 to 30 weight percent based on activated alumina and calcium chloride to reduce the content of the impurity to less than 50 ppm; and employing said hydrogen chloride having less than 50 ppm of said impurity in said oxychlorination of methane.

* * * * *